United States Patent [19] [11] 4,188,465
Schneider et al. [45] Feb. 12, 1980

[54] STABILIZED UREASE COMPOSITION

[75] Inventors: Walter Schneider, Weilheim; Albert Roder, Seeshaupt; Hans Mollering, Tutzing; Ingeborg Gutmann, Percha, uber Starnberg, all of Fed. Rep. of Germany

[73] Assignee: Boehringer Mannheim GmbH, Mannheim-Waldhof, Fed. Rep. of Germany

[21] Appl. No.: 781,222

[22] Filed: Mar. 25, 1977

[30] Foreign Application Priority Data

Mar. 25, 1976 [DE] Fed. Rep. of Germany ....... 2612726

[51] Int. Cl.$^2$ ............................................. G01N 31/14
[52] U.S. Cl. ...................................... 435/12; 435/188
[58] Field of Search ................... 195/63, 68, 103.5 U, 195/99

[56] References Cited

U.S. PATENT DOCUMENTS

| 3,119,751 | 1/1964 | Chaney | 195/103.5 U |
| 3,527,674 | 9/1970 | Deutsch | 195/63 |
| 3,542,649 | 11/1970 | Searcy | 195/103.5 U |
| 3,873,269 | 3/1975 | Kraffczyk et al. | 195/103.5 U |

Primary Examiner—Alvin E. Tanenholtz
Attorney, Agent, or Firm—Sprung, Felfe, Horn, Lynch & Kramer

[57] ABSTRACT

Stabilized urease compositions are provided comprising urease and, as a stabilizing agent, a mixture of glutathione, ethylenediamine-tetraacetic acid, and citrate, preferably in a weight ratio of 1:0.5–5:0.5–3:0.5–3.

14 Claims, No Drawings

STABILIZED UREASE COMPOSITION

The present invention is concerned with a stabilized urease composition, specifically one which is stabilized against loss of activity.

The enzyme urease splits urea, with the formation of carbonic acid and ammonia. It is available commercially in a relatively poorly purified form. In the crude state, urease is sufficiently storage-stable but in a purified state the stability decreases considerably and even at a specific activity of about 25 to 100 U/mg., the stability is unsatisfactory. Although there is a need for a highly purified enzyme, especially for clinical urea determination, it was hitherto not possible to provide a stable commercial preparation because of the insufficient stability. Commercially available urease with a specific activity of about 100 U/mg. already loses about 50% of its activity after storage for half a year in a refrigerator. Storage at ambient temperature or in dissolved form leads to a much more rapid loss of activity.

Attempts have already been made to increase the stability of the purified enzyme by variation of the buffer pH value, of the ionic strength and of the nature of the buffer (maleate, citrate, ethylenediamine-tetraacetic acid or phosphate) or by the addition of sulphhydryl group-containing compounds, such as cysteine and mercaptoethanol. However, all these attempts were unsuccessful. Only with twice crystallized bovine plasma albumin was it possible to achieve a certain prolongation of the half life time of the purified enzyme which, however, was insufficient (cf. K. R. Lynn, Biochim. Biophys. Acta, 146, 216/1967).

The present invention substantially overcomes this difficulty and provides a stabilized urease which, even in highly purified form, is sufficiently storage-stable to be a commercial proposition.

The compositions of the present invention comprise a stabilized urease which contains, as the stabilizing agent, a mixture of glutathione, ethylenediaminetetraacetic acid (EDTA) and citrate.

The stabilized urease according to the present invention can be, for example, in lyophilized form or in solution in a glycerol/water mixture.

Surprisingly, the mixture of the above-mentioned three substances is even able to stabilize highly purified urease, although it is known that the individual components of this mixture do not possess a stabilizing action.

Urease stabilized according to the present invention preferably contains the components urease, glutathione, EDTA and citrate in a weight ratio of 1:0.5–5:0.5–3:0.5–3. Preparations in this preferred composition range show, especially in the preferred activity range of about 50 to 300 U/mg., outstanding stability and still possess, for example, after lyophilization and storage for 12 weeks at 33° C., 100% of the initial activity before lyophilization. Without a stabilizing agent, even when lyophilized, the loss of activity is between 30 and 80%.

Even with urease preparations stabilized according to the present invention but outside of the preferred range, very good stabilizing effects can still be achieved.

Preferably, the enzyme preparation stabilized according to the present invention contains a urease which, before the addition of the stabilizer mixture, has been purified by treatment with a dextran. By means of this dextran treatment, it is possible approximately to double the activity of the enzyme. At the same time, a destabilizing impurity appears to be removed by dextran treatment so that urease preparations which have previously been subjected to a dextran treatment have an especially high stability after the addition of the stabilizer mixture. Treatment with the dextran can be carried out simply by stirring the dextran into an enzyme solution or by column chromatography. As dextran, it is preferable to use a cross-linked product with molecular sieve properties since, in this case, a desalting of the urease is achieved simultaneously with an enrichment of the enzyme and removal of a disturbing contaminant. Appropriate cross-linked or non-cross-linked dextran preparations are commercially available.

Urease stabilized according to the present invention is especially useful for the detection of urea. Therefore, the present invention also provides a reagent for the detection of urea which comprises urease stabilized according to the present invention, together with a system for the detection of ammonia.

Numerous systems for the detection of ammonia are known and these can be employed for the reagent according to the present invention provided that they do not contain any components which disturb the reaction catalyzed by the urease or the urease itself. Such a system for the detection of ammonia can comprise a pH indicator, for example bromothymol blue, which, by color change or the like, indicates an increased pH value due to ammonia formation. Such a system can be used, for example, for test papers or test films for the detection of urea in the blood or serum. Urease stabilized according to the present invention is so stable that it can be used for the impregnation of paper, film or similar carrier materials or for the production of reactive layers, together with a binding agent, on such carriers. When such a carrier or such a layer additionally contains a pH indicator, then urea can be determined by simple color change.

Another preferred system for the determination of ammonia within the scope of the reagent according to the present invention comprises glutamate dehydrogenase (GlDH), reduced nicotinamide-adenine dinucleotide (NADH) and buffer, and possibly also stabilizing agents for GlDH and/or NADH. Examples of such stabilizing agents include organic sulphhydryl compounds or adenosine diphosphate.

Another detection system which can be used makes use of Berthelot's indophenol reaction, this system comprising phenol or salicylic acid, together with sodium nitroferric cyanide and sodium hypochlorite.

The following Examples are given for the purpose of illustrating the present invention:

EXAMPLE 1

Commercially available urease with a specific activity of about 100 U/mg. was dissolved in water, applied to cross-linked dextran gel and subsequently lyophilized. The lyophilized preparation was then subjected to a stability test by storage at 33° C.

In a second batch, the above-described experiment was repeated but the enzyme treated with cross-linked dextran was mixed with glutathione, sodium citrate and EDTA in a weight ratio of 1:1:1:1. The lyophilization and storage were then repeated as in the first experiment.

In the first experiment without the addition of the stabilizing agent, the activity yield after lyophilization was 20%. After storage for 6 weeks at 33° C., the measured reactivity was less than 1%.

In the second experiment with the stabilizing agent according to the present invention, the activity after lyophilization was 100% and after storage for 6 weeks at 33° C. was still 100%. When storage under the given conditions was continued for 3 months, 100% of the initial activity before the lyophilization was again measured.

EXAMPLE 2

Commercially available urease with a specific activity of about 100 U/mg. was dissolved in water, mixed with glutathione, sodium citrate and EDTA in a weight ratio of 1:1:1:1 and lyophilized without dextran treatment. The lyophilisate was found to contain 100% of the initial activity.

The lyophilisate was then stored at 33° C. After 6 weeks storage, the activity was still 95% of the initial value.

EXAMPLE 3

From commercially available urease, there was obtained, by repeated crystallization and treatment with dextran, a urease with a specific activity of about 1500 U/mg. The preparation thus obtained was mixed with glutathione, sodium citrate and EDTA in a weight ratio of 1:3:3:3. The stability upon storage at 33° C. corresponded to that of the urease with an activity of 100 U/mg.

EXAMPLE 4

Test film for the detection of urea in the blood or serum:

| Components: | |
|---|---|
| polyvinyl acetate propionate dispersion (propiofan 70 D) | 45.0 g. |
| 1.93% aqueous solution of sodium alginate | 10.0 g. |
| dioctyl sodium sulphosuccinate | 0.5 g. |
| stabilized urease (dissolved in 10 ml. water) | 10000 U |
| bromothymol blue (dissolved in 5 ml. methanol nd 5 ml. water) | 0.25 g. |
| disodium hydrogen phosphate stabilized with glutathione, sodium citrate and EDTA (weight ratio 1:1:1:1) | 0.9 g. |

The components are well mixed and adjusted with 1 N hydrochloric acid to pH 6.0. The mass is coated in a layer thickness of 250μ on to a polyvinyl chloride film and dried for 60 minutes at 60° C. Dropping on of urea-containing blood or serum and wiping off thereof after 90 seconds gave the following color reactions:

20 mg.% urea—yellow
60 mg.% urea—yellow-green
100 mg.% urea—green
200 mg.% urea—dark green.

After 3 days at 60° C., this test film reacts practically unchanged.

A test film of the same composition and produced in the same manner which, however, instead of urease stabilized according to the present invention, contains an unstabilized urease of the same activity, initially shows practically the same reaction color but, after 3 days at 60° C., is no longer sufficiently reactive.

It will be understood that the specification and examples are illustrative but not limitative of the present invention and that other embodiments within the spirit and scope of the invention will suggest themselves to those skilled in the art.

Whereas in the foregoing examples sodium citrate was used, citrates of other cations compatible with urease e.g. alkali metal, earth alkali metal or amino cations likewise may be used.

What is claimed is:

1. Stabilized urease composition comprising urease of a specific activity of from 25–1500 U/mg and, as a stabilizing agent, a stabilizing mixture of glutathione, ethylenediamine-tetraacetic acid and citrate, wherein said citrate is present in stabilizingly effective amount.

2. Urease composition a claimed in claim 1, wherein said composition contains urease, glutathione, ethylenediaminetetraacetic acid and citrate in a weight ratio of 1:0.5–5:0.5–3:0.5–3.

3. Urease composition as claimed in claim wherein said urease is dextran pre-tested urease.

4. Urease composition as claimed in claim 1 wherein said urease is in lyophilized form.

5. Urease composition as claimed in claim 1 wherein said urease is in the form of a solution in a glycerol/water mixture.

6. Reagent for the detection of urea comprising a stabilized urease as claimed in claim 1, and a system for the detection of ammonia.

7. Reagent as claimed in claim 6 additionally containing a binding agent, carrier and buffer substance.

8. Reagent as claimed in claim 6 additionally containing a stabilizer for the system for the detection of ammonia.

9. Reagent as claimed in claim 6 comprising a carrier paper or carrier film impregnated with the stabilized urease and the system for the detection of ammonia or coated on in the form of a binding agent-containing layer.

10. Reagent as claimed in claim 6 wherein the system for the determination of urea contains at least one pH indicator and optionally a wetting agent and/or buffer.

11. Reagent as claimed in claim 6 wherein the system for the determination of ammonia comprises glutamic acid dehydrogenase, an alpha-ketoglutarate, reduced nicotinamide-adenine dinucleotide, adenosine diphosphate and a buffer.

12. Reagent as claimed in claim 6 wherein the system for the determination of ammonia comprises phenol or salicylic acid, sodium nitroferric cyanide and sodium hypochlorite.

13. Process for preparing a stabilized urease composition which comprises adding to urease of a specific activity of from 25–1500 U/mg, stabilizingly effective amounts of a stabilizing mixture of glutathione, ethylenediamine-tetraacetic acid and citrate, wherein said citrate is present in stabilizingly effective amount.

14. Process as claimed in claim 13 wherein said urease is treated with dextran prior to the addition of said mixture.

\* \* \* \* \*